United States Patent [19]
Schifano

[11] Patent Number: 5,591,173
[45] Date of Patent: Jan. 7, 1997

[54] SCHIFANO OBSTETRIC SCISSORS

[75] Inventor: Michael Schifano, 5525 N. Stanton, El Paso, Tex. 79912

[73] Assignee: Michael Schifano, El Paso, Tex.

[21] Appl. No.: 281,935

[22] Filed: Jul. 28, 1994

[51] Int. Cl.[6] .................................................. A61B 17/42
[52] U.S. Cl. .................................... 606/120; 606/157
[58] Field of Search ............................... 606/119, 120, 606/157, 86, 87, 88

[56] References Cited

U.S. PATENT DOCUMENTS

| | | | |
|---|---|---|---|
| 2,060,724 | 11/1936 | Carroll | 606/120 |
| 2,614,788 | 10/1952 | Woodward | 606/157 |
| 3,150,666 | 9/1964 | Averbach | 606/120 |
| 4,428,374 | 1/1984 | Auburn | 606/120 |
| 4,819,636 | 4/1989 | Gerich | 606/157 |

*Primary Examiner*—Michael A. Brown
*Attorney, Agent, or Firm*—Hill, Steadman & Simpson

[57] ABSTRACT

An obstetric scissors for clamping and severing an umbilical cord in a simplified manner is provided. Also, a method for severing an umbilical cord after clamping the umbilical cord with clamps is provided. The method provided severs an umbilical cord using an obstetric scissors having a pair of handles for actuating a pair of mounted clamps and cutting edges at an end thereof. The method has the steps of mounting a pair of clamps to a pivot pin and a pair of clamp holders of an obstetric scissors, positioning the obstetric scissors about the periphery of an umbilical cord such that the clamps impinge upon the umbilical cord, applying a force to the pair of handles of the obstetric scissors to compress the umbilical cord with the pair of clamps and continuing the application of such force so that after the umbilical cord is compressed by the clamps the cutting edges of the obstetric scissors can cut the umbilical cord while the clamps remain clamped on the umbilical cord on both sides of the obstetric scissors cutting edges.

14 Claims, 3 Drawing Sheets

SCHIFANO OBSTETRIC SCISSORS

BACKGROUND OF THE INVENTION

The present invention relates generally to scissors. More specifically, the present invention relates to obstetric scissors having integral clamps for severing an umbilical cord.

It is well known in the field of obstetrics that for every childbirth, the umbilical cord must be severed. Performing this commonplace operation, however, can be somewhat cumbersome for several reasons. First, the umbilical cord itself contains body fluids which, when the cord is severed, may spew forth in undesired directions. Thus, it is known to apply clamps to the umbilical cord which seal off the flow of any fluids therein.

Commonly, the physician or nurse must apply a first clamp, then apply a second clamp near the first clamp and cut the umbilical cord in the region between these two clamps. In this manner, the small clamped portion of the umbilical cord holds only a small amount of fluid such that when this portion is severed by scissors or hemostats, only a small portion of fluid potentially spews forth.

As a result of the above operation, specialized tools have been developed to aid in severing the umbilical cord. For example, different types of clamps have been designed that facilitate the operation of the above task. For instance, a common type of clamp is shaped in the form of a "V". The clamp has teeth on the inner portion to firmly clamp and seal off the umbilical cord. The two ends of the V-shaped clamp, away from the vertex, have a clamp plug and a clamp socket. Thus, when the V-shaped clamp is squeezed onto the umbilical cord, the plug and socket ends on the opposite portions of the V-shaped clamp engage and hold the clamp in position, sealing the umbilical cord.

While these different clamp designs aid in the performance of cutting the umbilical cord, it is still necessary for the practitioner to take the time to put a first clamp on the umbilical cord, add another clamp near the first clamp and then in a third step, cut the umbilical cord between the two clamps. Thus, the act of cutting the umbilical cord becomes a three-step process.

Accordingly, there has arisen a need for a method and an apparatus for cutting an umbilical cord with single-handed operation in a simpler manner.

SUMMARY OF THE INVENTION

The present invention provides a method and an apparatus for cutting an umbilical cord using a single apparatus in a single-handed operation.

To this end, in an embodiment, the present invention provides a method for severing an umbilical cord. The method has the steps of mounting at least one clamp to an obstetric scissors having cutting edges and a pair of handles, positioning the obstetric scissors about a periphery of the umbilical cord such that the at least one clamp impinges upon the umbilical cord, and applying a force to the pair of handles of the obstetric scissors to clamp and seal the umbilical cord with the at least on clamp and to subsequently sever the umbilical cord with the cutting edges while the at least on clamp is sealed about the umbilical cord.

In an embodiment, the method for severing an umbilical cord includes a further step of longitudinally mounting the at least one clamp to the outside of the obstetric scissors.

The present invention also provides an apparatus for severing a compressible body. The apparatus has a first handle with a first cutting edge, a second handle with a second cutting edge constructed and arranged to pivotably rotate with respect to the first handle, and clamping means operatively connected to at least one of the first handle and the second handle to seal the compressible body prior to severing same.

In an embodiment, the apparatus also has an integral spring-loaded shaft compression means operatively connected to the clamping means.

The present invention also provides a method for severing an umbilical cord having the steps of providing scissors with cutting edges, a pair of handles and a clamp, positioning the clamp about the umbilical cord such that the cord resides near a vertex of the clamp, applying a force to the clamp via the pair of handles of the scissors to close the clamp about the umbilical cord, and further compressing the pair of handles so that the cutting edges of the scissors subsequently sever the umbilical cord while the clamp remains clamped about the umbilical cord.

In an embodiment, the method of the invention further provides a second clamp connected to the clamp by a pair of connecting strips. In a further embodiment, a method of the present invention provides the step of severing the pair of connecting strips prior to severing the umbilical cord.

The present invention also provides a method for severing a clampable, fluid-containing conduit to minimize fluid spillage while severing. The method has the steps of clamping the conduit in at least two locations to provide a sealed region therebetween and severing the sealed region as a continuation of the clamping step.

In an embodiment, an obstetric scissors for severing an umbilical cord used in accordance with the method of the present invention is provided.

It is, therefore, an advantage of the present invention to provide a method and an apparatus for severing an umbilical cord in a simple manner using a single tool.

A further advantage of the present invention is to provide a method and an apparatus that is conducive for single-handed operation by a user.

Yet another advantage of the present invention is to provide a method and an apparatus for single-handedly cutting an umbilical cord that prevents excess spillage of body fluids from the umbilical cord while the same is being severed.

Also, an advantage of the present invention is to provide a method and apparatus for clamping a compressible body and cutting the body as a continuation of the clamping process.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides an obstetric scissors for severing an umbilical cord. Further, a method is provided for.

Figure 1:
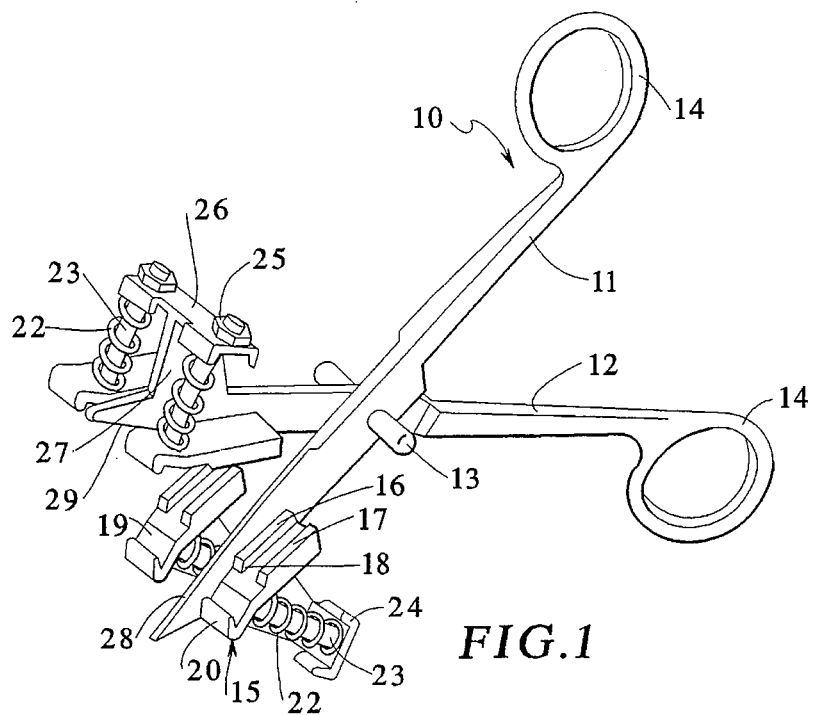
FIG. 1 illustrates a perspective view of an embodiment of the obstetric scissors of the present invention.

Now referring to embodiments of the present invention as illustrated in the figures, FIG. 1 illustrates an obstetric scissors 10 in perspective view. The scissors 10 has several parts. For example, in an embodiment, the scissors 10 is a hand-held and operated tool having a first handle 11 and a second handle 12 pivotally connected about a pivot pin 13 which acts as a fulcrum during the operation of the scissors 10. For convenience for the user, the scissors 10 is provided with finger holes 14 in each of the handles 11, 12. In addition to the pivot pin 13 providing a fulcrum for the scissors 10, the pivot pin 13 also provides a means for mounting clamps to the obstetric scissors 10.

Further, each of the handles 11, 12 have, at the end opposite the finger holes 14, a clamp holder 15 mounted thereto. The clamp holder 15 consists of several parts. In an embodiment, the clamp holder 15 has an inner guide wall 16 and an outer guide wall 17 and also provides a guide channel 18 therebetween. In addition, the clamp holder 15 has a clamp holder base 19 which is used to further secure a clamp on the obstetric scissors 10. Also, the clamp holder 15 has a clamp retaining flange 20 at its end.

As illustrated in FIG. 1, the clamp holder 15 is mounted to each side of each of the handles 11, 12. This provides a total of four clamp holders 15 on the scissors 10. Additional parts of the clamp holder 15 include a spring 22 mounted on a spring guide rod 23. The spring 22 is retained on the spring guide rod 23 by a spring retaining flange 24. A nut 25 is provided on the opposite end of the spring guide rod 23 to hold the spring retaining flange 24 which is part of the spring retainer 26 to a spring support member 27 which is an integral portion of each handle 11, 12. In addition, the scissors 10 further have a first cutting edge 28 on the first handle 11 and a second cutting edge 29 on the second handle 12.

Figure 2:
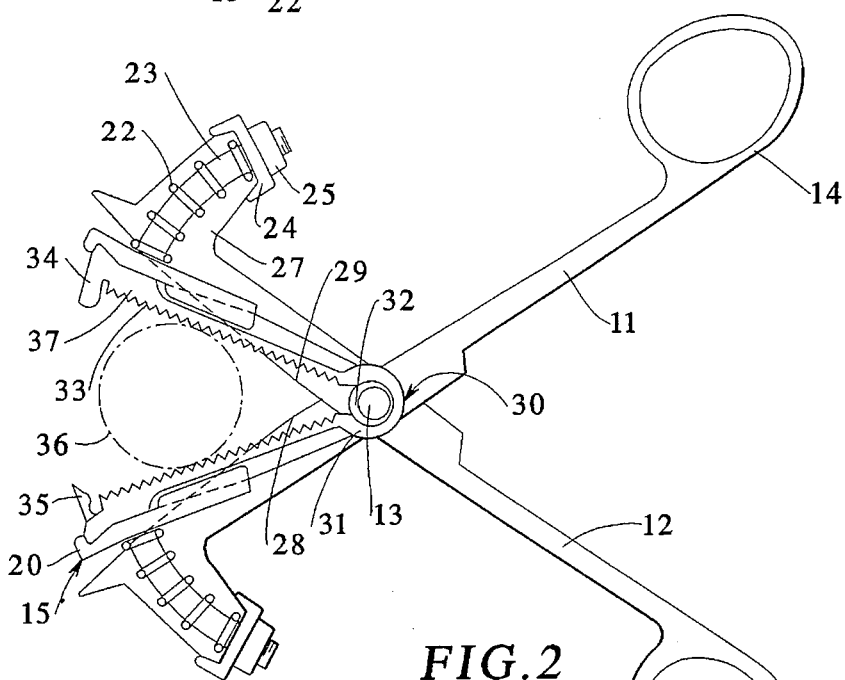
FIG. 2 illustrates a side view of an embodiment of the obstetric scissors of the present invention.

FIG. 2 also illustrates an embodiment of the obstetric scissors 10 of the present invention. The side view of FIG. 2 illustrates many of the same components already enumerated in the discussion of FIG. 1 wherein like numerals designate like parts.

To further illustrate an embodiment of the present invention, FIG. 2 shows a clamp 30 mounted to the obstetric scissors 10. The clamp 30 has a clamp ring 31 located generally at the vertex of the clamp 30. Within the clamp ring 31 is a clamp holding tongue 32. Since the clamp ring 31 has a larger diameter typically than the pivot pin 13 found on the obstetric scissors 10, the clamp holding tongue 32 urges toward the point of the vertex of the clamp 30 to firmly secure the clamp 30 to the pivot pin 13.

Also along the inner portion of the clamp 30 are clamp teeth 33 found on each leg of the clamp 30. The clamp 30 illustrated in FIG. 2 also has a socket end 34 on one leg of the clamp 30 and a plug end 35 on the other leg of the clamp 30. When the clamp 30 is in a fully closed position, the clamp teeth 33 are cooperatively engaged and the socket end 34 is cooperatively engaged with the plug end 35. In this manner, the clamp 30 can be securely closed about an umbilical cord 36, for example. As illustrated in FIG. 2, the clamp 30 is also provided with an end base 37 which resides in the clamp holder base 19 of the clamp holder 15 of the present invention.

Figure 3:
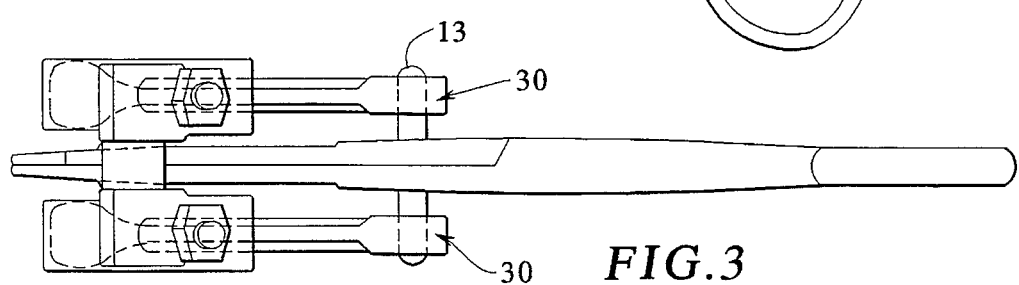
FIG. 3 illustrates a top view of an embodiment of the obstetric scissors of the present invention.

To further illustrate an embodiment of the present invention, FIG. 3 shows a top view of the obstetric scissors 10. As illustrated, a pair of clamps 30 are mounted in the clamp holder 15 of the obstetric scissors 10. The vertex end of the clamp 30, especially the clamp ring 31 is shown encircling the pivot pin 13 of the obstetric scissors 10.

The operation of severing an umbilical cord with the obstetric scissors 10 of the present invention will now be described with the assistance of FIGS. 2, 4 and 5 in the description thereof. First of all, FIG. 2 represents the obstetric scissors 10 in an open position surrounding an umbilical cord 36. As illustrated in FIG. 2, the clamp teeth 33 of the clamp 30 are tangential to the perimeter of the umbilical cord 36. Also as illustrated, the springs 22 are in their fully extended positions. The holder 15 is illustrated in its mounted position to the obstetric scissors 10.

As mentioned above, the clamp holding tongue 32 is urged against the pivot pin 13 as the clamp ring 31 encircles the pivot pin 13. At the other end of the clamp 30, the clamp base 37 is firmly seated within the clamp holder base 19 and abuts the clamp retaining flange 20 found at the end of each of the four clamps 15.

Figure 4:
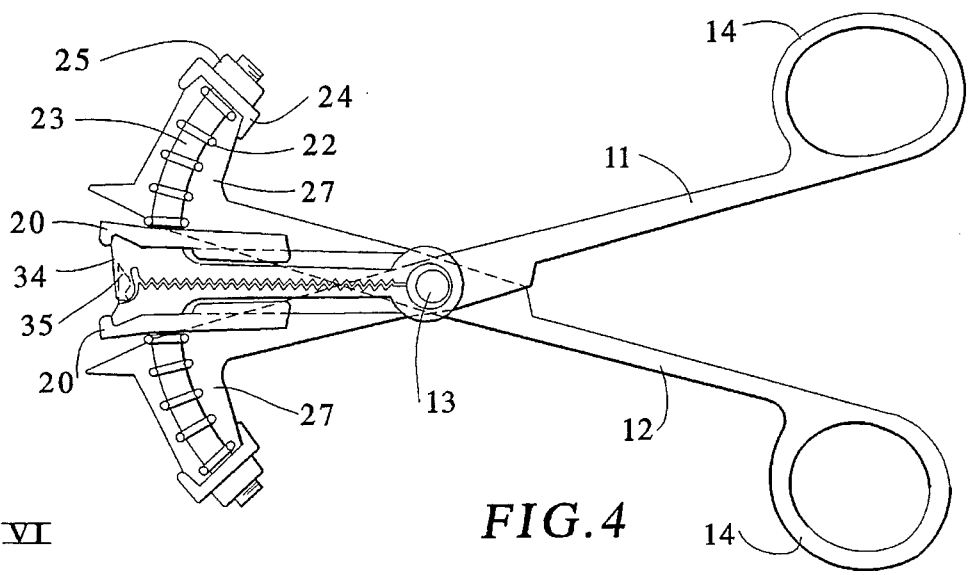
FIG. 4 illustrates a side view of an embodiment of the obstetric scissors of the present invention having a pair of clamps mounted thereto and with the scissors in a clamped but non-cutting position.

Now referring to FIG. 4 to continue the description of the operation of severing an umbilical cord with the obstetric scissors 10 of the present invention, the scissors 10 are in a second position. The second position illustrated shows that the clamp teeth 33 are cooperatively engaged with one another, and the socket end 34 and plug end 35 are also cooperatively engaged about the umbilical cord 36. The umbilical cord is not shown due to it being compressed between the clamp teeth 33 in a flattened and secured position.

In the operation of the present invention, a force is applied to the finger holes 14 of the first handle 11 and the second handle 12. This force acts about the fulcrum, which is the pivot pin 13, to cause closure of the open end of the obstetric scissors 10. This force enables the clamp teeth 33 to come together on the umbilical cord 36 and to cinch it off as shown in FIG. 4. However, at this point as illustrated in FIG. 4, the cutting edges 28 and 29 of the obstetric scissors 10 have not impinged upon the umbilical cord 36.

Figure 5:
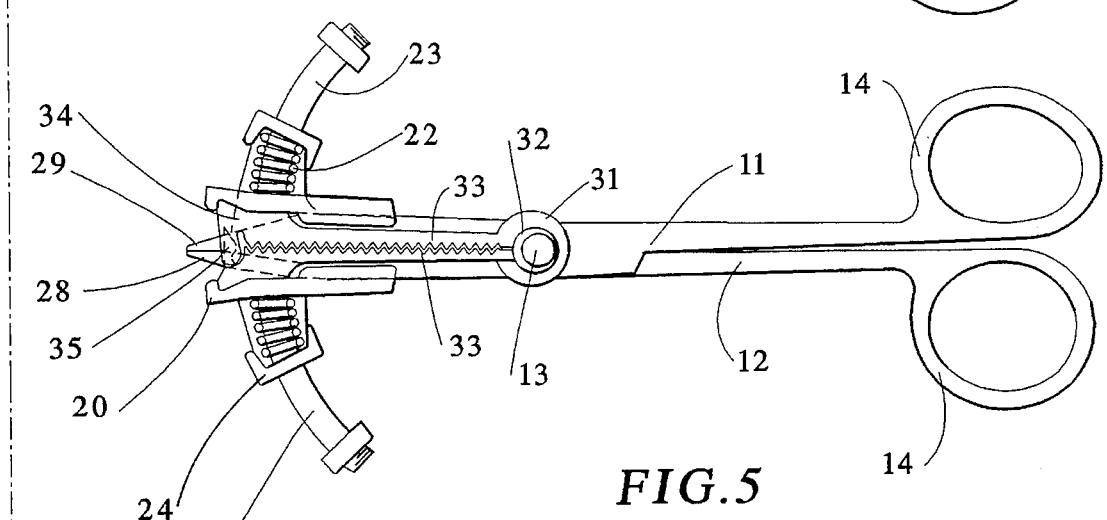
FIG. 5 illustrates an embodiment of the obstetric scissors of the present invention having a pair of clamps in a clamped position and with the scissors in a full-cutting position.

Now referring to FIG. 5, the operation of the present invention is furthered by continuing to apply a force to the finger holes 14 in order to fully close the open end of the obstetric scissors 10. By doing this, the cutting edges 28, 29 contact the umbilical cord 36 which has been compressed flat by the clamp 30 on each side of the obstetric scissors 10. Thus, the cutting edges 28, 29 are able to sever the portion of the umbilical cord 36 which is squeezed between the pair of clamps 30.

Thus, FIG. 5 illustrates the third and final position of a continuous operation in which the main positions, i.e. a first open position illustrated in FIG. 2, a second clamped yet non-cutting position illustrated in FIG. 4, and a clamped end cut position as illustrated in FIG. 5 are illustrated.

Figure 6:
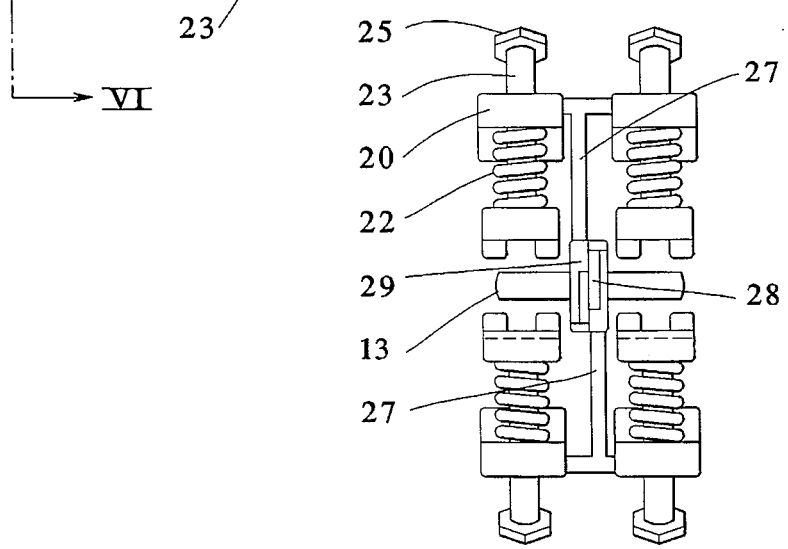
FIG. 6 illustrates an end view of an embodiment of the obstetric scissors of the present invention taken generally along the line VI—VI of FIG. 5 of the present invention.

In addition, FIG. 6 illustrates that the springs 22 are fully compressed in the final position of the operation of the obstetric scissors 10 of the present invention. Also, the cutting edges 29, 28 are shown fully together after severing the umbilical cord 36.

Figure 7:
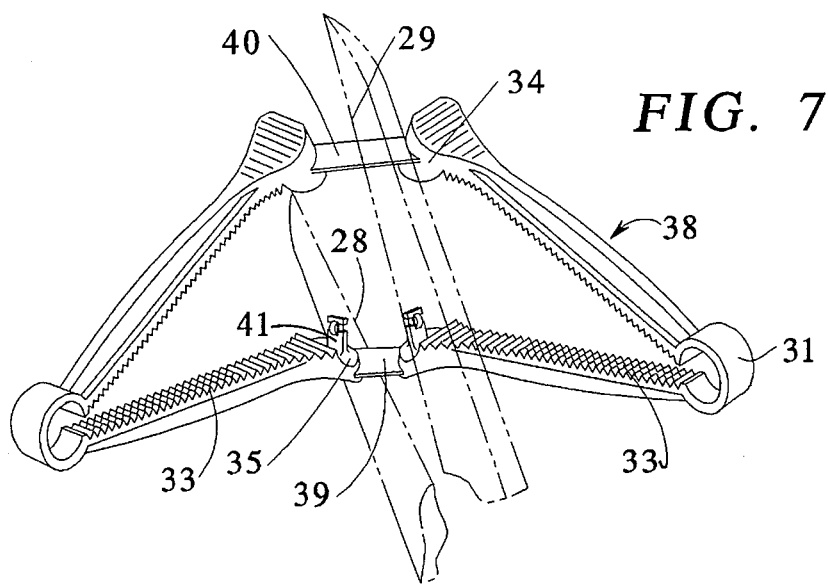
FIG. 7 illustrates a prospective view of another embodiment of a clamp for the present invention.

FIG. 7 illustrates another embodiment of obstetric scissors 10' the present invention showing a clamp 38 that has many of the same components enumerated in the discussion of FIG. 2 wherein like numerals designate like parts. For example, the clamp 38 has the clamp ring 31 and clamp teeth 33 proceeding therefrom to both the plug end 35 and the socket end 34. Also illustrated is the variation of this embodiment which entails a lower connecting strip 39 composed of a thin piece of like material connected between the plug ends 35 of the clamp 38. Also provided is an upper connecting strip 40 composed of a similar piece of like material connecting the socket ends 34 of the clamp 38. Further illustrated in FIG. 7 is a plug 41, which when the clamp 38 is actuated by the pair of cutting edges 28, 29, forms a locking bond with the socket end 34 to close the clamp 38 about an umbilical cord 36 as illustrated in FIG. 8.

Figure 8:
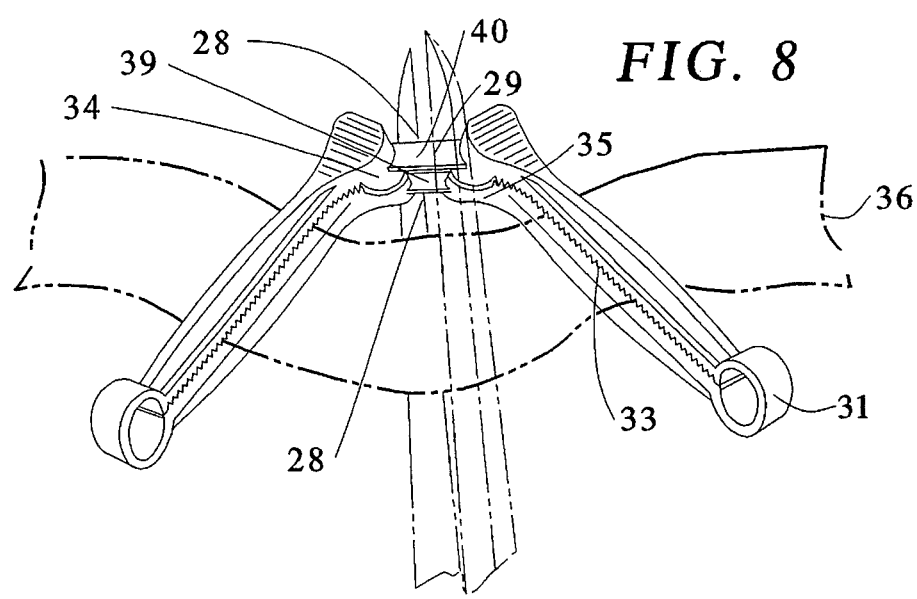
FIG. 8 illustrates another embodiment of the present invention having a clamp and scissors in a clamped, but non-cutting position.

Now referring specifically to FIG. 8, the present invention is shown having the clamp 38 fully clamped at two positions on the umbilical cord 36 to seal off any fluid flow therebetween. As illustrated, the cutting edges 28, 29 are actuated by the user to compress the clamp 38 about the umbilical cord 36. The cutting edges 28, 29 press against the connecting strips 39, 40 respectively to close the clamp 38 about the umbilical cord 36. However, at this point the cutting edges 28, 29 are not cutting the umbilical cord 36.

Figure 9:
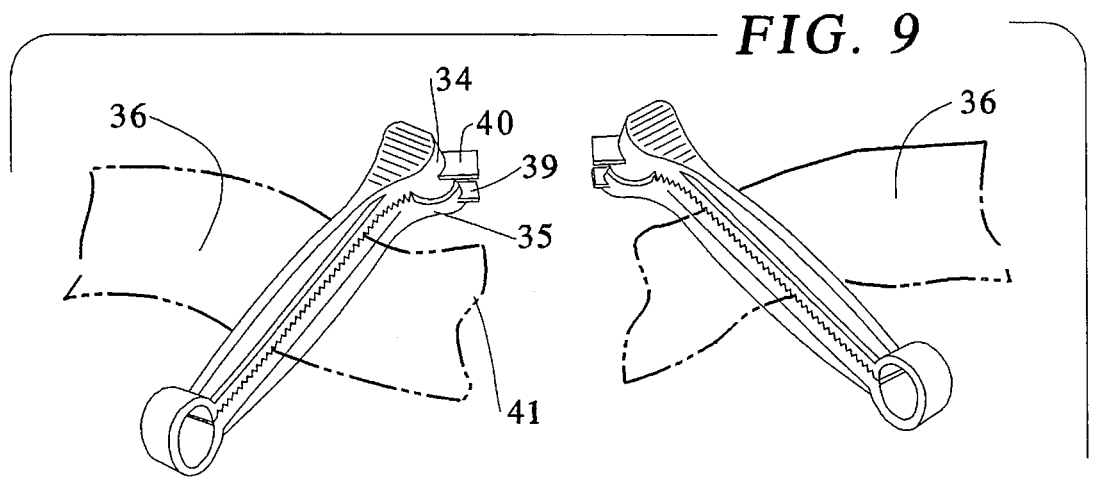
FIG. 9 illustrates another embodiment of the present invention in which the clamps are in a clamped position and the scissors have cut the umbilical cord and the clamp.

Further continuation of the process of severing the clamped umbilical cord 36 is illustrated in FIG. 9. As shown, the cutting edges 28, 29 of the obstetric scissors 10' are further closed about the clamp 38 to cut the connecting strips 39, 40 before cutting the umbilical cord 36. In this manner, the obstetric scissors 10' are able to close and seal the clamp 38 about the umbilical cord 36 and with the continuing applied force, the cutting edges 28, 29 sever the connecting strips 39, 40 and continue through to cut the clamped umbilical cord 36.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A method for clamping a compressible body prior to cutting the compressible body, the method comprising the steps of:

mounting at least one clamp onto a clamp holder base located on a scissors having a pair of handles, said scissors further including a support member having a spring retainer and a spring shaft having a spring encircling the spring shaft, one end of the spring shaft being operatively connected to the support member so that the retainer maintains the spring on the spring shaft and the other end of the spring shaft being operatively connected to the clamp holder base so that the spring urges the clamp holder base away from the spring retainer to clamp at least one clamp;

positioning the scissors about a periphery of the compressible body such that the at least one clamp impinges upon the compressible body;

applying a force to the pair of handles of the scissors to clamp and seal the compressible body with the at least one clamp; and further applying the force such that the scissors cut the compressible body while the at least one clamp is clamped and sealed about the compressible body.

2. The method of claim 1 further comprising the step of:

longitudinally mounting the at least one clamp to the scissors.

3. The method of claim 1 wherein the force applied to the pair of handles is a gripping force of an individual.

4. The method of claim 1 wherein the compressible body is an umbilical cord.

5. An apparatus for severing a compressible body, the apparatus comprising:

a first handle having a first cutting edge;

a second handle having a second cutting edge constructed and arranged to pivotably rotate with respect to the first handle;

a clamp holder base arranged adjacent to each of the cutting edges;

a support member having a spring retainer; and a spring shaft having a spring encircling the spring shaft, one end of the spring shaft being operatively connected to the support member so that the retainer maintains the spring on the spring shaft and the other end of the spring shaft being operatively connected to the clamp holder base so that the spring urges the clamp holder base away from the spring retainer to clamp at least one clamp to seal the compressible body prior to severing same.

6. The apparatus of claim 5 further comprising:

an integral spring-loaded shaft compression means operatively connected to the clamping means.

7. The apparatus of claim 5, further comprising:

a retaining lip on the clamp holder base.

8. The apparatus of claim 5, further comprising:

a guide channel in the clamp holder base.

9. A method for severing an umbilical cord, the method comprising the steps of:

providing scissors having cutting edges, a pair of handles, a clamp, a clamp holder base, a support member having a spring retainer, and a spring shaft having a spring encircling the spring shaft, one end of the spring shaft being operatively connected to the support member so that the retainer maintains the spring on the spring shaft and the other end of the spring shaft being operatively connected to the clamp holder base so that the spring urges the clamp holder base away from the spring retainer to clamp the clamp;

positioning the clamp about the umbilical cord such that the cord resides near a vertex of the clamp;

applying a force to the clamp via the pair of handles of the scissors to close the clamp about the umbilical cord; and further compressing the pair of handles so that the cutting edges of the scissors subsequently sever the umbilical cord while the clamp remains clamped about the umbilical cord.

10. The method of claim 9 further comprising the step of:

providing a second clamp connected to the clamp by a pair of connecting strips.

11. The method of claim 10 further comprising the step of:

severing the pair of connecting strips prior to severing the umbilical cord.

12. An apparatus for holding and actuating at least one clamp, the apparatus comprising:

a clamp holder base;

a support member having a spring retainer; and a spring shaft having a spring encircling the spring shaft, one end of the spring shaft being operatively connected to the support member so that the retainer maintains the spring on the spring shaft and the other end of the spring shaft being operatively connected to the clamp holder base so that the spring urges the clamp holder base away from the spring retainer to clamp at least one clamp.

13. The apparatus of claim 12 further comprising:

a retaining lip on the clamp holder base.

14. The apparatus of claim 12 further comprising:

a guide channel in the clamp holder base.

\* \* \* \* \*